United States Patent [19]

Burbidge

[11] 4,144,126

[45] Mar. 13, 1979

[54] CELL CULTURE METHOD
[75] Inventor: Colin Burbidge, Crawley, England
[73] Assignee: Beecham Group Limited, Great Britain
[21] Appl. No.: 826,761
[22] Filed: Aug. 22, 1977

Related U.S. Application Data

[63] Continuation-in-part of Ser. No. 686,097, May 13, 1976, abandoned.

[30] Foreign Application Priority Data

May 21, 1975 [GB] United Kingdom ............... 21998/75

[51] Int. Cl.² ........................... C12K 7/00; C12K 9/00
[52] U.S. Cl. ........................................ 195/1.1; 195/1.8
[58] Field of Search ................................. 195/1.8, 1.1

[56] References Cited

U.S. PATENT DOCUMENTS

| | | | |
|---|---|---|---|
| 3,821,087 | 6/1974 | Knazek et al. | 195/1.8 |
| 3,873,423 | 3/1975 | Munder et al. | 195/1.8 |

*Primary Examiner*—Sam Rosen
*Attorney, Agent, or Firm*—Jacobs & Jacobs

[57] ABSTRACT

A method for culturing animal cells in vitro in a monolayer by supporting the cells on the surface of a solid porous matrix and contacting the cells so supported with a liquid medium in the form of a foam. As the foam comes into contact with the matrix it breaks down and flows over the surface of the cells as a film, leaving gas in the interstitial spaces.

16 Claims, 1 Drawing Figure

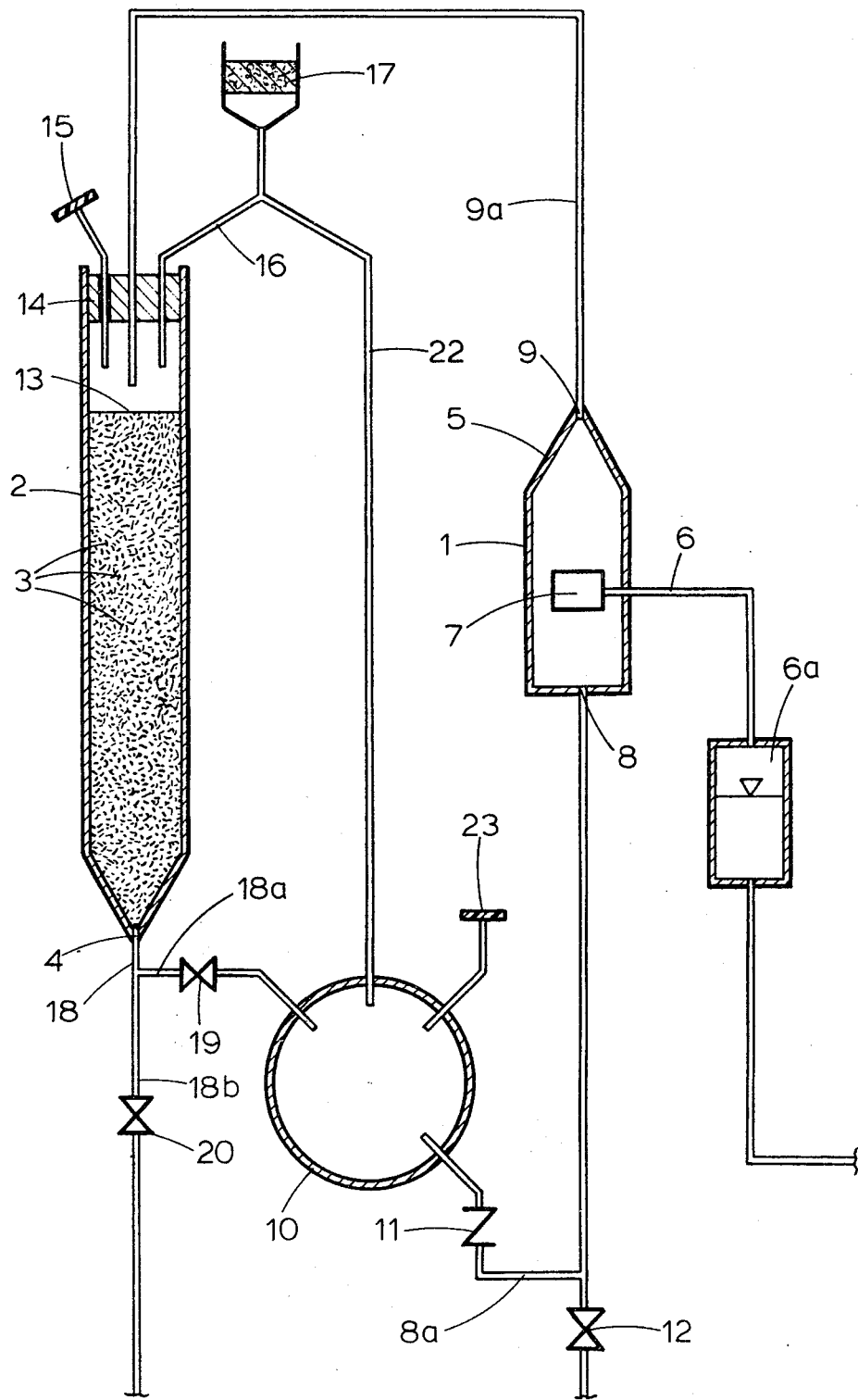

CELL CULTURE METHOD

This application is a continuation-in-part of my application Ser. No. 686,097 filed May 13, 1976 and now abandoned.

The invention relates to an improved method for the monolayer culture of animal cells in vitro and an apparatus to operate the method.

There are two chief methods for culturing discrete cells or micro-organisms in vitro: firstly as a suspension in a stirred tank reactor and secondly as a monolayer attached to a supporting surface. Generally, a suspension culture is only suitable for established cell lines, cells of the lymphocytic type including normal lymphocytes, tumor cells such as Burkitt lymphoma cells and leukaemic myoblasts. Cells forming sheets or strands such as fibroblasts and epithelial cells unless transformed require a solid support upon which to grow and it is with the latter method of culturing that the present invention is concerned.

Laboratory scale monolayer culture is a simple process in which cells are supported and grown on the inside walls of a static or rotating bottle. It is well known that for mass monolayer culture, cells must be provided with a large surface area. The rotating bottle has been adapted for large scale production by linking together a number of culture vessels so that culture medium may be continuously pumped through a series of bottles. However, methods employing this type of apparatus are labour intensive, since subculturing is often required, and the apparatus itself is costly, large and mechanically complex.

An apparatus for providing a large surface within a single culture vessel is described by W. Wohler et. al. in the Journal of Experimental Cell Research Volume 92 1972, page 571, and is the subject of West German Offenlegungsschrift No. 2,300,567. The apparatus consists of a conical flask containing a high surface area matrix such as a mass of glass beads. The cells are applied to the matrix which is submerged in the culture medium and the medium is continuously replenished.

The disadvantages of this submerged culture technique are:

(1) that the apparatus required to maintain the medium characteristics is complex; and
(2) that due to differences in concentration in the medium covering the cells it does not give in general as good growth conditions as the rotating bottle, in which cells are covered by a thin film of growth medium.

The present invention is based on the discovery of a novel method of supplying a thin film of nutrient medium to discrete cells in a monolayer.

According to this invention there is provided a method for culturing animal cells wherein a monolayer of the cells supported on the surface of a solid porous matrix, is contacted wtih a film of liquid nutrient medium derived from the breakdown of a foam, which is generated from nutrient medium and a gas.

In the method of this invention, a monolayer of cells is attached to at least part of the solid porous matrix, for example by steepin the matrix in a suspension of the cells in a liquid medium, allowing the cells to settle on the matrix and subsequently draining the suspension medium. Nutrient medium in the form of a foam is then supplied to the matrix at a sufficiently fast rate to prevent the matrix from drying out, whilst the cells are maintained at a suitable physiological temperature (i.e. 35°-38° C.). As the foam comes into contact with the matrix, it breaks down and flows as a thin film throughout the matrix, over the surface of the cells, while leaving the gas in the interstitial spaces. The medium flowing from the matrix may be run to waste or, where suitable, recycled. The cells are cultured until the matrix is covered with a sufficiently large monolayer of cells. The cells are then washed to remove nutrient medium optionally using a film derived from a foamed wash medium. The cells are then removed by any standard method, for example by trypsinization optionally with gentle agitation of the matrix, and then collected.

This method is suitable for culturing those cells derived from animals, including mammals, birds, amphibia, fish and insects, which grow in sheets in vitro. Examples of such cells are those derived from Epithelial tissue, Connective tissue, Muscle tissue, Nervous tissue and Lymph tissue. In particular, the method is applicable to culturing skin and muscle fibroblasts derived from mammals including man.

The matrix used in this invention is porous. The interstitial spaces of the porous matrix must be sufficiently large, (a) to accommodate the cell monolayers; (b) to allow the culture medium to flow as a thin film across the monolayer surface, while retaining gas in spaces; and (c) to allow the removal of the cells.

The surface of the porous matrix of this invention must be capable of adhering the cells to be cultured and capable of releasing the cells when the culture process is complete. It is well known that animals cells in particular adhere well to surfaces which carry high densities of sodium ions. They therefore adhere to materials which tend to acquire a negative charge and thus bind sodium ions. The matrix may be made from a material to which cells adhere or be made up from an inert support and coated with such a material. Suitable materials include plastics, materials such as nylon, polycarbonate, polystyrene, epoxyresins, silicone rubber, cellulose acetate, cellulose nitrate, cellophane and P.T.F.E., polyethylene terephthalate, polyformaldehyde, fluorinated ethylene-propylene co-polymer, polyphenylene oxide, polypropylene mica, carbon, collagen, insoluble inert metal oxides, phosphates, silicates or carbides, silicon carbide, inert metals such as stainless steel, aluminium, titanium or palladium, or ceramics or glass. We have found that different cell types adhere to the matrices with differing degrees of tenacity. For exaple some cell lines adhere so well to some of the above types of support that it becomes difficult to remove the cells when harvesting is required. Thus it is sometimes necessary to modify the characteristics of the surface by applying a coating of a material less adhesive to cells, which eases their removal. Coating materials which we have found render cells more readily removable from matrix surfaces are polyfluorinated hydrocarbons such as polytetrafluoroethylene, or silicones such as polymethylhydrogensiloxane. On the other hand a surface of low adhesive capacity may be altered to give better adhesion by the application of a suitable coating.

Thus the particular surface coating which is employed will depend upon the type of cells to be cultured and whether harvesting from the matrix is required. A suitable coating or combination of coating for any particular application may be determined empirically.

Materials which we have found in particular to be suitable for the formation of matrices for use in this invention include polycarbonate, nylon 6, nylon 11, nylon 12, glass, polyformaldehyde, polypropylene and 2,6-dimethylphenyleneoxide. Coated matrices which we have in particular found to be suitable for the formation of matrices for use in this invention include polycarbonate coated with polytetrafluoroethylene, silicone, polymethylhydrogensiloxane; glass coated with silicone, polytetrafluoroethylene or stearic acid; or polyethyleneterephthalate, nylon 6, nylon 11 and nylon 12, each coated with polytetrafluoroethylene.

In any specific application of this method the particular material of choice may be determined by incidental factors such as the method by which the matrix is to be sterilized.

The matrix may be made from one or more macroreticular solid pieces. Such matrices may be for example, a solid foam formed in a material capable of supporting cells, e.g. a plastics material such as nylon, polycarbonate, polystyrene or an inorganic material such as silica gel.

Alternatively the matrix may be in the form of a plug of fibrous materials such as a metal wire wool, a plastics wool or glass wool. In these circumstances the material would be loosely packed in order to prevent any coalescence of the thin film flow into liquid drops submerging part of the matrix. A further type of matrix may take the form of a regular lattice of threads, such as net, made up from for example plastics, metallic, or glass thread.

In yet another embodiment the matrix may consist of a mass of regular or irregular solid or hollow granules made from or coated with the types of materials previously discussed. The shape and size of the granules is not critical. Regular shapes such as spheres or cylinders are preferred to irregular shapes, since it has been found that nylon cylinders were more suitable than the moulding chips from which they were prepared. Spheres are more suitable than cylinders since for a given volume, spheres have a higher surface area.

For spheres, suitable diameters are in the range 1–10mm, preferably in the range 2–4mm. The diameters of cylinders are suitably in the range 1–10mm, preferably 3–5mm; and the length of cylinders may be from 1–10mm, preferably 3–5mm. Particularly suitable cylinders have a diameter of 4mm and a length of 4mm. Matrices prepared from pieces of material smaller than the above range have small pore sizes and complete removal of cells is difficult; and larger pieces present a smaller surface area.

A nutrient medium used in the method of this invention must contain sources of readily assimilable carbon, nitrogen, and oxygen. The medium is buffered to the correct physiological pH range (6.5–8.0) and may be supplemented with metal salts such as Earle's salts, ascorbic acid, nonessential amino acids such as; alanine, asparagine, aspartic acid, glycine, glutamic acid, proline and serine, or a serum such as foetal bovine serum. Where necessary the medium may also contain antibiotics such as penicillin. When culturing mammalian cells, any medium normally employed for such cells may be used in this method. Suitable media include: Eagle's, Fischer's, Ham's, Leibovitz, McCoy's, Neumann and Tytell's, Puck's Swim's, Trowell's or Waymouth's medium, also 199, NCTC 109, NCTC 135, CMRL 1066, or RPML medium.

The foam may be generated in the medium by any standard method of foam generation, for example, by beating gas into the medium with one or more mechanical whisks. Alternatively the foam may be generated relying on gas dissolved in the medium. By using a cavitating pump in which an impeller rotates at high speed, areas of low pressure are set up in the liquid medium in which bubbles form thereby causing a foam. In yet another method, the gas may be introduced into liquid by a single or multiple, static or moving, gas inlets or with a sintered glass bulb.

The foam may be generated from any non-toxic gas or mixture of gases. The foam may be generated in the medium using a completely inert gas, and the aerobic conditions required for culturing the animal cells may be generated by subsequently introducing the required amount of oxygen into the system. We have also found that by introducing carbon dioxide into the culture system, an equilibrium is set up between the carbon dioxide in the gas phase and in the liquid phase. This equilibrium provides a buffering effect which assists in maintaining a uniform pH throughout the culture system. When the foam is first generated in the culture medium with an inert gas and then supplemented with a second gas, it is preferable that the second gas be introduced to the culture system at a point beyond which the foam has come into contact with the matrix and broken down, so as to prevent any deterioration of the foam. Alternatively, the foam may be generated directly using a gas required mixture containing oxygen and optionally carbon dioxide. In such circumstances an inert diluent gas must be included to prevent oxidizing conditions being set up within the culture which would be detrimental to the cells. Similarly where carbon dioxide is included we have found that the gas mixture preferably does not contain oxygen and carbon dioxide alone, since toxic effects are often observed and thus a diluent such as nitrogen should be added.

For the aerobic culture of mammalian cells (e.g. fibroblasts) mixtures containing from 1 to 15% v/v of oxygen and 99 to 85% nitrogen are suitable and a preferred mixture is one containing 10% oxygen and 90% nitrogen. In the case of foams for aerobic cultures generated from gas mixture also containing carbon dioxide suitable proportions are 7 to 10% v/v of oxygen 0.5 to 7.5% v/v of carbon dioxide made up to 100% with nitrogen. One preferred mixture contains 5% carbon dioxide, 10% oxygen and 85% nitrogen.

Of course the foam could be generated from a gas neither containing nor being supplemented with carbon dioxide and that the pH of the medium could be controlled by standard buffer system.

The foam may be stabilized by supplementing the medium with a non-toxic surfactant. Examples of surfactants which are useful in this way are sera such as foetal bovine serum; bactopeptone, lipoic acid, linoleic acid, methylcellulose, carboxymethylcellulose, PLURONIC F68 and TWEEN 80. [PLURONIC and TWEEN are Registered Trade Marks]. Some media, for example, McCoy's medium, Ham's medium and media NCTC 109, NCTC 135, CMRL 1066 already contain surfactants such as bactopeptone, lipoic acid, linoleic acid and Tween 80. We have found that although these media can be made to foam and flow as a thin film, additional surfactant may advantageously be added in order to obtain satisfactory culturing. The additional surfactant employed may be a further amount of the surfactant already present in the medium or any of the different surfactants previously noted.

When the foam has been generated, it is supplied to the solid matrix. In order to achieve this supply, the foam generator is situated so as to supply foam to at least part of the matrix. The transference of the foam from the generator to the matrix is achieved either by pumping the foam by using for example a peristaltic pump, or making use of the flow imparted to the foam by the generator, e.g., where the foam is generated in a cavitating pump or by the injection of gas. Alternatively the point of generation of the foam may be situated above the point of application so that the foam may flow to the matrix through ducts, under the influence of gravity.

A preferred characteristic required of a foam used in the method of this invention is that it should be sufficiently stable to arrive at the matrix without having undergone any substantial collapse. Foams of low stability which collapse between the point of generation and application tend to set up a liquid flow which submerges the matrix and the advantages of the film culture are not achieved. This undesired liquid flow may be drained from the foam for recycling or run to waste before it arrives at the matrix, but this tends to reduce the efficient use of medium.

The characteristics of any particular foam will be determined by the proportion of surfactant employed, and the size of the gas bubbles introduced into the liquid. The stability of the foam is enhanced by increasing the proportion of the surfactant and decreasing the size of the gas bubbles. The particular foam of choice will depend upon the distance the foam must travel from the generator to the point of application. These features will in turn depend upon the particular apparatus employed for carrying out the method of this invention, but may quite easily be determined by generating a foam and observing its degree of collapse in transfer. We have found that a foam generated using a nutrient medium containing at least 0.05% additional surfactant in which gas bubbles have mean diameters within the range 0.1 to 2mm inclusive may travel through a distance of at least 175cm without any substantial collapse of foam. A preferred foam for use under these particular circumstances contains 0.1% surfactant or 5% or 10% of serum and bubbles of substantially 0.5mm mean diameter.

The rate at which the foam is supplied to the matrix should be sufficient to contact substantially all the cell monolayer on the matrix. The rate at which the foam is supplied is dependent upon the type of matrix employed and the cross-sectional area which it presents to the foam. We have found that a suitable rate of flow of foam to supply to a matrix made up of spheres having diameters in the range 2-4mm or cylinders having diameters of 1-10mm and lengths of 1-10mm, is between 20 and 320cm$^3$hr$^{-1}$ per cm$^2$ of bed cross-sectional area.

The cells may be washed after culturing and before removal with any suitable physiological buffer solution supplemented by surfactant, e.g. phosphate buffered brine supplemented with methylcellulose.

The method of this invention is particularly useful for the preparation of cell products such as interferon, or for the production of virus antigens suitable for inclusion in vaccines.

Thus the cells which are supported on the matrix in a monolayer, prior to being contacted with a film of liquid nutrient medium according to the invention, may be treated with an interferon inducer or with an infective virus. Such a treatment of the cells may be performed either before or after the cells are supported on the matrix. The treatment may also advantageously be performed using a film derived from the breakdown of a foam.

Thus the invention also provides a method for the treatment of cells which method comprises contacting a monolayer of mammalian cells supported on the surface of a solid porous matrix with a liquid medium containing either an interferon inducer or an infective virus, the liquid medium being in the form of a film derived from the breakdown of a foam generated from liquid medium and a gas.

Interferon may be induced in such cells on incubation with inducing substances such as viruses, virus particles, double stranded ribonucleic acid (ds RNA) of viral origin and synthetic double stranded ribonucleic acids (ds RNA). Double stranded ribonucleic acids having this capacity may be isolated from viruses infecting certain fungi such as Penicillia and Aspergilli as described in, for example, British Patent No. 1170929, Banks et. al. Nature 218 542 (1968) and in our British Patent No. 1300259.

Most suitably the interferon inducer employed in the method of this invention is a double stranded ribonucleic acid of viral origin, as found in virus particles infecting Penicillia, for example, P. chrysogenum (British Pat. No. 1170929); P. stoloniferum (Banks et. al., Nature 218 542 (1968)); P. cyaneofulvum (Banks et. al., Nature 213 155 (1968)) and in Aspergilli, for example, A. niger and A. foetidus (British Pat. No. 1300259). Preferably the ds RNA is as found in viral particles which infect P. chrysogenum (British Pat. No. 1170929).

For viral infection, the particular species from which the cell is obtained depends on the type of vaccine which is to be prepared. Virus antigens for incorporation into pharmaceutical vaccines are produced from the cells of higher primates such as monkey or man but are preferably obtained from human cells. Virus antigens for incorporation into veterinary vaccines are produced from a suitable animal species.

The cells are infected by incubating the cells with the infective virus. Examples of viruses which may be produced by this method for the preparation of pharmaceutical vaccines include Rabies, Measles, Mumps, German Measles, Polio, myelitis, Adenovirus, Yellow fever, Parainfluenza, Herpes, Cytomegalovirus, Influenza, Parainfluenza Hepatitis, Infectious mononucleosis and Respiratory syncytial virus.

Examples of viruses which may be produced for the preparation of veterinary vaccines include Mareks disease, Parainfluenza, Adenovirus, Distemper, Cat leukaemia, Infectious bovine rhinotracheitis, Infectious bronchitis, Foot and Mouth Disease, Calf diarrhoea, Equine rhinopheumonitis, Pseudorabies, Infectious laryngotracheitis, Swine vesicular, Transmiscible gastroenteritis.

The types of cells which are suitable for use in this method are those animal cells which are capable of growing in sheets, for example, fibroblasts and epithelial cells as previously discussed. For convenience skin and muscle fibroblasts are preferred.

Prior to induction of infection treatment, the cells are attached to at least part of the matrix and optionally grown to a confluent sheet by the method previously described. For this purpose any of the media previously discussed are suitable. Where fibroblasts are used, a particular medium is Eagle's medium supplemented with bovine foetal serum, bovine brain extract, nonessential amino acids, Earle's salts, ascorbic acid and an antibiotic and buffered with sodium bicarbonate.

For interferon induction, interferon is induced in the cell sheets by either submerging the matrix in an induction medium or introducing the induction medium as a thin film derived from the breakdown of a foam generated in an induction medium supplemented with a surfactant. Suitably this induction incubation is performed at a temperature within the range generally suitable for cell growth, i.e. 35° to 38° C. preferably about 37° C. This induction incubation may be carried out for a period of between one and three hours. We have found that two hours is a convenient period. The induction medium is a solution comprising the ds RNA in any of the conventional culture media optionally supplemented by any of the surfactants previously discussed. It is generally most convenient to dissolve the ds RNA in the same medium as employed for the cell culture. Where fibroblast cells are used, a preferred induction medium is one in which the ds RNA is dissolved in minimum essential (Eagle's) medium supplemented with an antibiotic and DEAE dextran and buffered to a physiological pH with sodium bicarbonate.

For viral infection, the cells are then infected by either submerging the matrix with an infection medium or introducing the infection medium as a thin film derived from the breakdown of a foam generated in an infection medium supplemented with a surfactant. The infection medium is a solution comprising the virus in any of the conventional culture media optionally supplemented with any of the surfactants previously discussed. It is generally most convenient to suspend the virus in the same medium as employed for the cell culture. Where fibroblast cells are used, a preferred infection medium is one in which the virus is suspended in minimum essential (Eagle's) medium supplemented with an antibiotic and DEAE dextran and buffered to a physiological pH with sodium bicarbonate. Suitably this infection incubation is performed at a temperature within the range generally suitable for cell growth, i.e. 35° to 38° C. preferably about 37°. The infection incubation may be carried out for a period of between one and three hours. We have found that two hours is a convenient period.

After the induction of infection period, the cells are washed free of infection medium with phosphate buffered saline either by immersion or by supplying the saline as a thin film and a collection medium is supplied to the cell sheet as a thin film for a period of between 6-25 hours, preferably 16-20 hours for the collection of interferon and between 3 to 7 days for the collection of virus. The collection medium may be any of the typical culture media as previously discussed. It is generally most convenient to use the same medium as used for cell culture, in the case of fibroblast cells, particularly suitable collection medium is minimum essential (Eagle's) medium and supplemented with foetal bovine serum, and an antibiotic and buffered with sodium bicarbonate to a physiological pH. The collection is carried out in the temperature range generally employed for the culture of cells, i.e. 35° to 38° C. preferably 37° C. After the collection period, the circulation of the collection medium is stopped, the matrix drained and medium containing interferon or virus is then collected. The interferon or virus content of the solution may then be assayed and the interferon or virus isolated by any of the standard methods.

In another of its aspects this invention provides apparatus in which this method may be performed.

Accordingly this invention provides apparatus comprising a vessel containing a solid porous matrix which permits the adherence of cells, a foam generator located to supply foam to at least part of the surface of the solid porous matrix and means for removing liquid from the vessel.

The vessel suitable for use in this invention may be a tower or trough of circular or rectangular cross-section, or in the shape of a hollow cone, invert cone or sphere. The vessel will have an inlet through which the matrix can be introduced, and an outlet from the foam generator through which the foam is supplied to the matrix. The vessel may also be provided with a further inlet for introducing the suspension of cells. This may take the form of a self-sealing rubber diaphragm or a standard steam sterilizable inlet port. In order to ensure that the characteristics of the medium remain in the desired range, the vessel may be provided with pH and/or $pO_2$ sensitive electrodes.

The vessel may also be provided with a gas outlet optionally through a sterile filter to allow the escape of gas from the foam. The vessel may also be provided with an additional gas inlet positioned suitably beyond the point at which the foam collapses onto the matrix so that the influx of gas does not break up the foam. Medium is supplied to the foam generator from a reservoir suitably by gravity feed, or optionally by pumps.

The efflux of medium from the vessel may be run to waste or return by pumping where necessary to the medium reservoir.

Apparatus in accordance with this invention will now be described by way of example with reference to the accompanying FIG. 1, which is a schematic diagram of apparatus according to this invention.

Referring to FIG. 1, a cell culture apparatus in accordance with this invention may be seen to comprise, a foam generator, 1; a vessel in the form of a cylindrical tower, 2; containing a solid porous matrix, 3; the vessel having an outlet, 4; as means for removing liquid.

In this particular embodiment the foam generator, 1; consists of a cylindrical housing, 5; a gas inlet pipe, 6; which is attached at one end to a flow meter, 6a; and which towards the other end passes into the housing through the side wall, and terminates in a sintered glass disc, 7. The generator, 1; also has a liquid inlet, 8; at one end of the housing and a foam outlet, 9; at the other end of the housing. The inlet, 8; is connected to a liquid reservoir, 10; via a supply pipe, 8a; having a non-return valve, 11. The liquid supply pipe in this embodiment may be drained by valve, 12; situated between the non-return valve and the foam generator. The foam outlet, 9; is connected to one end of a foam supply pipe, 9a; which terminates within the vessel, 2; above the top surface, 13; of the solid porous matrix, 3.

In this embodiment the tower, 2; contains a matrix, 3; of small plastic cylinders. The tower is closed at the top end by a tightly fitting bored bung, 14; through which the foam supply pipe, 9a; passes. The tower tapers at the lower end to form an outlet, 4. The tower, 2; also has an inlet for cell suspensions, in the form of a self-sealing rubber diaphragm, 15; and a gas outlet pipe, 16; terminating in a bacterial filter, 17. The outlet, 4; is connected to one end of a withdrawal pipe, 18. The withdrawal pipe, 18; is divided into two parts, one part, 18a; of which returns via a valve, 19; to the liquid reservoir, 10; and the other part, 18b; forms a drainage outlet through the valve, 20. The reservoir, 10; to which medium is returned has a gas outlet pipe, 22; and a liquid inlet in the form of a self-sealing rubber diaphragm, 23. The gas outlet, 22; in this embodiment joins the gas outlet pipe, 16; from the vessel, 2; below the bacterial filter, 17.

In order to use the device, the tower, 2; is filled with a convenient quantity of polycarbonate cylinders, the bored bung, 14; is inserted into the tower and the apparatus assembled. The entire apparatus is then sterilized. The apparatus is then placed in a constant temperature environment (ca 37° C.) and allowed to come to ambient temperature. Cells suspended in sufficient medium to immerse the matrix are introduced to the tower, 2; via the self-sealing diaphragm, 15; and the apparatus is allowed to stand for between 2 and 20 hours to allow the cells to settle onto the matrix. Nutrient medium is introduced to the reservoir, 10; through the self-sealing rubber diaphragm, 23; and is allowed to flow into the foam generator, 1; via pipe 8a. A sterile gas is introduced into the generator at a rate metered by flowmeter, 6a; which causes the medium to foam. The foam is swept along the pipe, 9; to the top of the matrix by the gas flow. As the foam arrives at the matrix it breaks down and the liquid medium flows over the matrix surface. At the same time the valve, 20; is opened to allow the efflux of the suspension medium at a rate sufficient to allow its replacement by nutrient medium derived from the foam, and to prevent the cell layer becoming dry. When the suspension medium has been replaced by nutrient medium derived from the foam, the drainage valve, 20; is closed and the valve, 19; is opened so that the medium returns to the reservoir, 10. The nutrient medium is recycled until a colony of cells of the required size has been established. The gas supply is then shut off, and the valve, 19; closed. The reservoir, 10; and the foam generator are drained of nutrient medium and filled with wash medium. The gas supply is restarted. The cells are washed with a thin film of wash medium until free of culture medium. The effluent is either allowed to run to waste through the valve, 20; or is recycled to the reservoir, 10; through the valve, 19. The supply of foam is then stopped and the cells are removed from the matrix suitably by filling the culture vessel with a cell release solution such as trypsin. The matrix may be optionally agitated gently to assist in freeing the cells by slowly passing gas through the matrix from below through the pipe, 18; while keeping valve 19 closed.

The suspension of cells is then withdrawn through the drainage valve, 20; while keeping valve 19 closed and valve 20 open.

The apparatus may be provided optionally with a vapour trapping condenser below the bacterial filter, 17; and an optional additional gas supply situated so as to introduce gas at a point below which the withdrawal pipe, 18; divides into the two parts 18a and 18b.

The invention is illustrated by the following Examples.

EXAMPLE 1

The apparatus as described in specification having a vessel 2 of 3.5 cm diameter was filled to a depth of 25 cm with moulded poly-carbonate cylinders 4 mm in diameter and 4 mm long. The entire apparatus was sterilized by autoclaving at 15 psi for 30 minutes.

The apparatus was then allowed to cool to room temperature and with valves 19 and 20 closed an inoculum of $3.6 \times 10^{27}$ L929 mouse fibroblast cells suspended in 100 cm³ of growth medium were introduced via the inlet point 15 using a hypodermic syringe. The growth medium used was Eagle's medium, supplemented with Earle's salts, 10% Foetal bovine serum, non-essential amino acids, ascorbic acid and penicillin/streptomycin.

The medium was buffered with 2.2 g of sodium bicarbonate per liter and contained the pH indicator, phenol red.

The inoculated apparatus was allowed to stand for 20 hours at 37° in order to let the cells settle and attach themselves to the packing.

When the cells had settled on to the porous matrix the valve 19 was opened slightly to allow the liquid to drain from the vessel and at the same time a gas mixture containing 10% oxygen + 85% nitrogen + 5% carbondioxide, was supplied to the foam generator at a rate of 25 cc/min so that foam arrived at the top surface of the porous matrix as the liquid present drained away. The rate of flow of medium through valve 19 was controlled so that the medium in which the cells had been suspended is replaced by medium derived from the foam and the cells on the matrix did not become dry. When the medium in which the cells had been suspended was completely drained from the tower the valve 19 was completely opened and the rate of flow of liquid through the column was controlled by the rate of breakdown of foam at the surface of the matrix.

The foam was allowed to circulate for 72 hours.

The supply of gas to the generator 1 was stopped and valve 19 closed. The reservoir 10 and foam generator 1 were drained through valve 12. With valve 12 closed the reservoir 10 was filled with a wash medium 0.15 molar brine buffered to pH 7.3 with phosphate and supplement with 0.1% methyl cellulose. The wash medium was caused to foam and pass through the vessel 2 and run to waste through valve 20 via pipe 18b, until the cells were free from the last traces of the red nutrient medium. The valve 20 was closed and trypsin/versene solution at 37° C. was introduced into the vessel via the inlet 15 to immerse the porous matrix, and after 10 minutes the packing the solution was gently agitated for five minutes by introducing via valve 20, a slow gentle stream of sterile air. The cells having been suspended in the buffer as a result of the agitation are drained from the vessel 2, via valve 20. A further portion of trypsin/versene buffer was added to remove any remaining cells.

The number of cells harvested was determined by counting them using a haemocytometer.

| Total cells inoculated | | $3.6 \times 10^7$ |
|---|---|---|
| Cells harvested | (i) in drained growth medium and saline wash buffer | $0.8 \times 10^7$ |
| | (ii) in Trypsin/versene | $5.25 \times 10^7$ |
| Total | | $6.05 \times 10^7$ |

EXAMPLE 2

Using the method of example 1 human fibroblasts were cultured and interferon produced as follows:

A 5 cm × 15 cm matrix of 4 mm silicone treated polycarbonate beads packed into a cylindrical glass tower was inoculated with $2.5 \times 10^7$ human skin/muscle fibroblasts. The cells were added as a suspension in growth medium comprising minimum essential medium (Eagle) with Earle's salts supplemented with 10% foetal bovine serum, non-essential amino acids, ascorbic acid, fibroblast growth factor. penicillin/streptomycin and 0.88 g/l sodium bicarbonate.

The inoculated matrix was incubated and left to stand overnight at 37° C. The suspension medium was slowly drained and incubation with nutrient commenced by supplying a mixture of 5% carbon dioxide in sterile air to liquid in the foam generator. This mixture was adjusted to give the correct pH level (7.0–7.2) in the medium. The medium circulation was continued for 48 hours.

Medium was allowed to accumulate in the matrix which was then washed by overlaying the beads and medium and slowly draining liquid from the base of the matrix. Induction medium was added in a similar manner and comprised minimum essential (Eagle) medium (MEM) supplemented with Earle's salts, sodium bicarbonate, penicillin/streptomycin, 5 ug/ml ds RNA and 100 ug/ml DEAE dextran. This was left in contact with the cells for 2 hours at 37° C. and then washed off with PBS as before. The PBS wash was displaced by collection medium (MEM, sodium bicarbonate, penicillin/streptomycin and 1% foetal bovine serum). Tower left overnight at 37° C. in this condition when medium was drained off and found to contain human interferon (3,300 international units).

EXAMPLE 3

Using the method of example 1, human fibroblasts were cultured as follows:

A 3.5 cm × 25 cm matrix of 4 mm polycarbonate beads, which had been sprayed with PTFE aerosol spray (Fisons) and packed into a cylindrical glass tower, were inoculated with $8 \times 10^6$ human skin/muscle fibroblasts. The cells were added as a suspension in growth medium comprising minimum essential medium (Eagle's) with Earle's salts supplemented with 10% foetal bovine serum, non-essential amino acids, penicillin/streptomycin and 0.88 g/l sodium bicarbonate.

The inoculated matrix was incubated at 37° C. overnight. The suspension medium was slowly drained and circulation of nutrient commenced by supplying a mixture of air and carbon dioxide to liquid in the foam generator. This mixture was adjusted to give the correct pH level (7.0–7.2) in the medium. The medium circulation was continued for 75 hours.

The supply of gas to the generator 1 was stopped and valve 19 closed. The reservoir 10 and foam generator 1 were drained through valve 12. With valve 12 closed the reservoir 10 was filled with a wash medium 0.15 molar brine buffered to pH 7.3 with phosphate and supplemented with 0.1% methyl cellulose. The wash medium was caused to foam and pass through the vessel 2 and run to waste through valve 20 via pipe 18b, until the cells were free from the last traces of the red nutrient medium. The valve 20 was closed and trypsin/versene solution at 37° C. was introduced into the vessel via the inlet 15 to immerse the porous matrix, and after 10 minutes the packing and solution was gently agitated for 5 minutes by introducing via valve 20 a slow stream of sterile air. The cells having been suspended in the buffer as a result of the agitation are drained from the vessel 2, via valve 20. The agitation was repeated using 0.15 M brine buffered to pH 7.3 with phosphate. A further portion of trypsin/versene buffer was added followed by a further portion of brine both of which were agitated to remove any remaining cells.

| Total cells inoculated | | $8 \times 10^6$ |
|---|---|---|
| Cells harvested | (i) in drained growth medium and saline wash buffer | $0.5 \times 10^6$ |
| | (ii) in 1st trypsin/versene treatment | $10.7 \times 10^6$ |
| | (iii) in 1st agitated saline wash | $1.95 \times 10^6$ |
| | (iv) in 2nd trypsin/versene treatment | $2.48 \times 10^6$ |
| | (v) in 2nd agitated saline wash | $4.13 \times 10^6$ |
| | | Total $19.8 \times 10^6$ |

In the following table examples are given of the method of the invention employed to culture various human fibroblasts using differing matrices.

The abbreviations used therein have the following meanings:

1000: Flow 1000 human skin and muscle fibroblasts
7000: Flow 7000 human foreskin fibroblasts
12000: Flow 12000 human epithelial nasal mucosal cells
meth: methylcellulose
F.G.F.: Fibroblast growth factor
P.C.: poly carbonate
VIT.C.: Ascorbic acid
N 6: nylon 6
N 11: nylon 11
N 12: nylon 12
PET: polyethylene terephthalate
PET(O): oxygenated polyethylene terephthalate
PPO: polyphenyleneoxide
PP: polypropylene
PE: polyethylene
PF: polyformaldehyde
FEP: Fluorinated ethylene propylene co-polymer
P.T.F.E.: poly tetrafluoroethylene
S: silicone
Sil: silicone
D.C. Sil: Dow Corning Silicone 1107
Stearic: Stearic acid
A: air
N: nitrogen
O/N: overnight Inoculation and Harvest are measured in: Number of cells $\times 10^7$

| Example | Cells | Serum | Additives | Packing | Gas | Inoculation | Harvest | Growth period in days | Ratio | Attachment Period |
|---|---|---|---|---|---|---|---|---|---|---|
| 4 | 1000(P25) | 10% | — | PC | A/N/CO$_2$ | ≦2.5 | 1.78 | 4 | — | O/N |
| 5 | 1000(P25) | 10% | 0.1% meth | PC | A/N/CO$_2$ | 2.5 | 2.07 | 4 | — | O/N |
| 6 | 1000(P26) | 10% | — | PC | A/N/CO$_2$ | 1.35 | 1.15 | 4 | — | O/N |
| 7 | 1000(P26) | 10% | — | PC | A/N/CO$_2$ | 1.35 | 1.26 | 4 | — | O/N |
| 8 | 1000(P28) | 10% | — | PC | A/N/CO$_2$ | 1.7 | 1.35 | 8 | — | O/N |
| 9 | 1000(P28) | 10% | — | PC | A/N/CO$_2$ | 1.7 | 1.71 | 11 | 1 | O/N |
| 10 | 1000(P29) | 10% | — | N 11 | A/N/CO$_2$ | 1.9 | 1.46 | 8 | — | O/N |
| 11 | 1000(P29) | 10% | — | PET(O) | A/N/CO$_2$ | 1.6 | 1.61 | 8 | 1 | O/N |
| 12 | 1000(P29) | 10% | — | PC/S | A/N/CO$_2$ | 1.6 | 1.72 | 8 | 1.08 | O/N |
| 13 | 1000(P29) | 10% | — | PC/PTFE | A/N/CO$_2$ | 1.6 | 3.05 | 8 | 1.9 | O/N |
| 14 | 7000(P24) | 10% | — | GLASS | A/N/CO$_2$ | 1.5 | 0.72 | 9 | — | O/N |
| 15 | 7000(P24) | 10% | — | GLASS/S | A/N/CO$_2$ | 1.5 | 0.74 | 9 | — | O/N |
| 16 | 7000(P24) | 10% | — | GLASS/PTFE | A/N/CO$_2$ | 1.5 | 0.59 | 9 | — | O/N |
| 17 | 7000(P25) | 10% | — | PC/PTFE | A/N/CO$_2$ | 1.4 | 2.09 | 8 | 1.49 | O/N |

-continued

| Example | Cells | Serum | Additives | Packing | Gas | Inoculation | Harvest | Growth period in days | Ratio | Attachment Period |
|---|---|---|---|---|---|---|---|---|---|---|
| 18 | 7000(P25) | 10% | — | PC/PTFE | A/N/CO$_2$ | 1.4 | 2.9 | 8 | 2.07 | O/N |
| 19 | 7000(P26) | 10% | — | PC/PTFE | A/N/CO$_2$ | 1.8 | 1.92 | 4 | 1.07 | O/N |
| 20 | 7000(P26) | 10% | — | PC/PTFE | A/N/CO$_2$ | 1.8 | 2.51 | 6 | 1.4 | O/N |
| 21 | 7000(P26) | 10% | — | PC/PTFE | A/N/CO$_2$ | 1.8 | 2.80 | 5 | 1.56 | O/N |
| 22 | 7000(P26) | 10% | — | PC/PTFE | A/N/CO$_2$ | 1.8 | 5.18 | 11 | 2.88 | O/N |
| 23 | 7000(P26) | 10% | — | PC/PTFE | A/N/CO$_2$ | 1.8 | 3.64 | 7 | 2.02 | O/N |
| 24 | 7000(P27) | 10% | — | PC/PTFE | A/CO$_2$ | 1.05 | 2.94 | 4 | 2.8 | O/N |
| 25 | 7000(P27) | 10% | — | PC/PTFE | A/CO$_2$ | 1.25 | 2.95 | 4 | 2.36 | O/N |
| 26 | 1000(P37) | 10% | — | PC/PTFE | A/CO$_2$ | 0.9 | 0.99 | 1 | 1.10 | O/N |
| 27 | 1000(P37) | 10% | — | PC/PTFE | A/CO$_2$ | 0.9 | 1.18 | 2 | 1.31 | O/N |
| 28 | 1000(P37) | 10% | — | PC/PTFE | A/CO$_2$ | 0.9 | 2.27 | 5 | 2.52 | O/N |
| 29 | 1000(P37) | 10% | — | PC/PTFE | A/CO$_2$ | 0.9 | 2.11 | 8 | 2.34 | O/N |
| 30 | 1000(P37) | 10% | — | PC/PTFE | A/CO$_2$ | 0.9 | 2.47 | 9 | 2.75 | O/N |
| 31 | 1000(P39) | 10% | — | PC/PTFE | A/CO$_2$ | 0.8 | 1.98 | 4 | 2.47 | O/N |
| 32 | 1000(P39) | 10% | — | PC/PTFE | A/CO$_2$ | 0.8 | 2.13 | 4 | 2.66 | O/N |
| 33 | 1000(P40) | 10% | — | N6/PTFE | A/CO$_2$ | 0.6 | 0.75 | 4 | 1.25 | O/N |
| 34 | 1000(P40) | 10% | — | N11/PTFE | A/CO$_2$ | 0.6 | uncountable | 4 | — | O/N |
| 35 | 1000(P40) | 10% | — | N12/PTFE | A/CO$_2$ | 0.6 | uncountable | 4 | — | O/N |
| 36 | 1000(P40) | 10% | — | PC/PTFE | A/CO$_2$ | 0.6 | 0.94 | 4 | 1.57 | O/N |
| 37 | 7000(P32) | 10% | — | PF | A/CO$_2$ | 1.0 | 1.3 | 4 | 1.3 | O/N |
| 38 | 7000(P32) | 10% | — | PF/PTFE | A/CO$_2$ | 1.0 | 0.335 | 4 | — | O/N |
| 39 | 7000(P32) | 10% | — | PC/PTFE | A/CO$_2$ | 1.0 | 1.07 | 7 | 1.07 | O/N |
| 40 | 7000(P31) | 10% | — | PET/PTFE | A/CO$_2$ | 0.8 | 0.96 | 4 | 1.20 | O/N |
| 41 | 7000(P31) | 10% | — | PET(O)/PTFE | A/CO$_2$ | 0.8 | 0.88 | 4 | 1.10 | O/N |
| 42 | 7000(P31) | 10% | — | PC/PTFE | A/CO$_2$ | 0.8 | contaminated | — | — | O/N |
| 43 | 1000(P23) | 10% | — | PET/PTFE | A/CO$_2$ | 1.25 | 0.89 | 4 | — | O/N |
| 44 | 1000(P23) | 10% | — | PET(O)/PTFE | A/CO$_2$ | 1.25 | 1.27 | 4 | 1.02 | O/N |
| 45 | 1000(P23) | 10% | — | PC/PTFE | A/CO$_2$ | 1.25 | 1.26 | 4 | 1.01 | O/N |
| 46 | 1000(P24) | 10% | — | PET/PTFE | A/CO$_2$ | 1.375 | induced | 7 | — | O/N |
| 47 | 1000(P24) | 10% | — | PET(O)/PTFE | A/CO$_2$ | 1.375 | induced | 8 | — | O/N |
| 48 | 1000(P24) | 10% | — | PC/PTFE | A/CO$_2$ | 1.375 | induced | 9 | — | O/N |
| 49 | 1000(P26) | 10% | — | FEP | A/CO$_2$ | 1.0 | 0.25 | 4 | — | O/N |
| 50 | 1000(P26) | 10% | — | PPO | A/CO$_2$ | 1.0 | 0.685 | 4 | — | O/N |
| 51 | 1000(P26) | 10% | — | PPO/PTFE | A/CO$_2$ | 1.0 | 0.91 | 4 | — | O/N |
| 52 | 1000(P26) | 10% | — | PC/PTFE | A/CO$_2$ | 0.725 | induced | 9 | — | O/N |
| 53 | 1000(P26) | 10% | — | PC/PTFE | A/CO$_2$ | 0.725 | induced | 8 | — | O/N |
| 54 | 1000(P26) | 10% | — | PC/PTFE | A/CO$_2$ | 0.725 | induced | 10 | — | O/N |
| 55 | 12000(P23) | 10% | — | PC/PTFE | A/CO$_2$ | 1.2 | 1.24 | 4 | 1.03 | O/N |
| 56 | 12000(P23) | 10% | — | FEP | A/CO$_2$ | 1.2 | 0.41 | 4 | — | O/N |
| 57 | 12000(P23) | 0 | 0.1% Meth | FEP | A/CO$_2$ | 0.8 | 0.59 | 4 | — | O/N |
| 58 | 12000(P24) | 5% | 5% FGF | PC/PTFE | A/CO$_2$ | 0.95 | 0.77 | 3 | — | O/N |
| 59 | 12000(P24) | 10% | — | PC/PTFE | A/CO$_2$ | 1.05 | 0.79 | 3 | — | O/N |
| 60 | 12000(P24) | 10% | — | PC/PTFE | A/CO$_2$ | 1.05 | 1.18 | 3 | 1.12 | O/N |
| 61 | 12000(P25) | 5% | — | PC/PTFE | A/CO$_2$ | 0.8 | 0.675 | 4 | — | 2½hr. |
| 62 | 12000(P25) | 5% | — | PC/PTFE | A/CO$_2$ | 0.8 | 0.503 | 4 | — | 16hr. |
| 63 | 12000(P25) | 5% | — | PC/PTFE | A/CO$_2$ | 0.8 | 0.734 | 4 | — | 16hr. |
| 64 | 1000(P30) | 5% | — | PC/PTFE | A/CO$_2$ | 1.0 | 2.03 | 4 | 2.03 | 2½hr. |
| 65 | 1000(P30) | 5% | — | PC/PTFE | A/CO$_2$ | 1.0 | 1.45 | 4 | 1.45 | 2½hr. |
| 66 | 1000(P24) | 10% | — | PC/PTFE | A/CO$_2$ | 1.375 | 1.23 | 4 | — | O/N |
| 67 | 1000(P24) | 10% | — | PC/PTFE | A/CO$_2$ | 1.375 | 1.175 | 4 | — | O/N |
| 68 | 1000(P25) | 5% | — | PC/PTFE | A/CO$_2$ | 0.925 | 0.57 | 4 | — | 3hr. |
| 69 | 1000(P25) | 5% | — | PC/PTFE | A/CO$_2$ | 0.925 | 0.42 | 4 | — | 5hr. |
| 70 | 1000(P25) | 5% | — | PC/PTFE | A/CO$_2$ | 0.925 | 0.13 | 4 | — | 7hr. |
| 71 | 1000(P25) | 5% | — | PC/PTFE | A/CO$_2$ | 0.925 | 0.21 | 4 | — | 9hr. |
| 72 | 1000(P27) | 10% | — | PP | A/CO$_2$ | 0.72 | 0.34 | 4 | — | 3hr. |
| 73 | 1000(P27) | 10% | — | PP | A/CO$_2$ | 0.72 | 0.39 | 4 | — | 5hr. |
| 74 | 1000(P28) | 5% | FGF | PP | A/CO$_2$ | 1.04 | 0.41 | 4 | — | 3hr. |
| 75 | 1000(P28) | 5% | FGF | PP | A/CO$_2$ | 1.04 | 0.53 | 4 | — | 3hr. |
| 76 | 1000(P28) | 5% | FGF | PP | A/CO$_2$ | 1.3 | 0.86 | 4 | — | 3hr. |
| 77 | 1000(P29) | 5% | FGF + VITC | PC | A/CO$_2$ | 1.2 | 0.91 | 4 | — | 3hr. |
| 78 | 1000(P29) | 5% | | PC | A/CO$_2$ | 1.2 | 0.53 | 4 | — | 3hr. |
| 79 | 12000(P25) | 5% | — | PC | A/CO$_2$ | 1.7 | induced | 3 | — | 3hr. |
| 80 | 12000(P26) | 5% | VITC | PC/Sil | A/CO$_2$ | 1.9 | 1.40 | 4 | — | 3hr. |
| 81 | 12000(P26) | 5% | VITC | PC/Sil | A/CO$_2$ | 1.9 | 1.46 | 4 | — | 3hr. |
| 82 | 1000(P26) | 5% | FGF/VITC | PC/DC.Sil | A/CO$_2$ | 2.5 | induced | 2 | — | 3hr. |
| 83 | 1000(P29) | 10% | — | PC/DC.Sil | A/CO$_2$ | 2.1 | 1.32 | 4 | — | — |
| 84 | 1000(P29) | 10% | — | PC/Sil | A/CO$_2$ | 2.1 | 1.29 | 4 | — | — |
| 85 | 1000(P29) | 10% | — | PC/PTFE/Sil | A/CO$_2$ | 2.1 | 1.62 | 4 | — | — |
| 86 | 1000(P31) | 5% | — | PC/Sil | A/CO$_2$ | 1.7 | 0.7 | 4 | — | 3hr. |
| 87 | 1000(P31) | 5% | — | GLASS/Stearic | A/CO$_2$ | 1.7 | 0.6 | 4 | — | 3hr. |
| 88 | 1000(P33) | 5% | FGF | PC/Sil | A/CO$_2$ | 1.7 | 1.13 | 4 | — | 3hr. |
| 89 | 1000(P33) | 5% | FGF | PC/Sil | A/CO$_2$ | 1.7 | 0.9 | 4 | — | 3hr. |
| 90 | 1000(p33) | 5% | FGF | PC/DC.Sil | A/CO$_2$ | 1.7 | 2.2 | 4 | 1.3 | 3hr. |
| 91 | 12000(P33) | 5% | VITC | PP | A/CO$_2$ | 1.7 | 2.06 | 4 | 1.21 | 3hr. |
| 92 | 12000(P33) | 5% | VITC | PE | A/CO$_2$ | 1.7 | 1.67 | 4 | 1.0 | 3hr. |
| 93 | 12000(P33) | 5% | VITC | PP | A/CO$_2$ | 1.7 | 1.79 | 4 | 1.05 | 3hr. |
| 94 | 1000(P35) | 5% | FGF/VITC | PP | A/CO$_2$ | 1.36 | 1.16 | 4 | — | 3hr. |
| 95 | 1000(P35) | 5% | FGF/VITC | PP | A/CO$_2$ | 1.36 | 0.58 | 4 | — | 3hr. |
| 96 | 1000(P35) | 5% | FGF/VITC | PE | A/CO$_2$ | 1.36 | 0.76 | 4 | — | 3hr. |
| 97 | 1000(P23) | 5% | FGF/VITC | PP | A/CO$_2$ | 1.78 | 0.896 | 4 | 0.54 | 3hr. |
| 98 | 1000(P23) | 5% | FGF/VITC | PP | A/CO$_2$ | 1.97 | induced | 2 | — | 3hr. |
| 99 | 1000(P23) | 5% | FGF/VITC/HEPES | PE | A/N$_2$ | 2.56 | 1.20 | 4 | 0.47 | 3hr. |

-continued

| Example | Cells | Serum | Additives | Packing | Gas | Inoculation | Harvest | Growth period in days | Ratio | Attachment Period |
|---|---|---|---|---|---|---|---|---|---|---|
| 100 | 1000(P24) | 5% | FGF/VITC | PC/DC.Sil | A/CO$_2$ | 1.45 | 2.45 | 4 | 1.69 | 3hr. |
| 101 | 1000(P24) | 5%/10% | FGF/VITC/Meth | PC/DC.Sil | A/CO$_2$ | 1.45 | 1.92 (2.38) | 4 | 1.32 (1.64) | 3hr. |

What we claim is:

1. In a method for culturing animal cells in a monolayer supported on the surface of a solid porous matrix the improvement comprising contacting said cells with a film of liquid nutrient medium derived from the breakdown of a foam which is generated from said nutrient medium and a gas leaving gas in interstitial spaces.

2. A method according to claim 1 wherein said matrix comprises solid granules.

3. A method according to claim 2 wherein said granules are cylindrical or spherical.

4. A method according to claim 2 wherein said granules are made of a plastic material, ceramics, glass, an inert metal; or an inert metallic oxide, phosphate, silicate, or carbide.

5. A method according to claim 1 wherein said cells are mammalian.

6. A method according to claim 5 wherein said cells are human.

7. A method according to claim 1 wherein the medium is supplemented with a non-toxic surfactant.

8. A method according to claim 1 wherein said gas contains up to 10% carbon dioxide.

9. A method according to claim 1 wherein the foam is sufficiently stable to be transported from its point of generation to its point of application to the matrix without substantial collapse.

10. A method according to claim 1 wherein said cells are treated with an interferon inducer or an infective virus prior to being contacted with said film of liquid nutrient medium.

11. In a method for producing interferon in vitro, the improvement which comprises contacting a monolayer of mammalian cells supported on the surface of a solid porous matrix with a liquid medium containing an interferon inducing substance, said liquid medium being in the form of a film derived from the breakdown of a foam generated from said liquid medium and a gas leaving gas in the interstitial spaces; and thereafter separating the interferon.

12. A method according to claim 11 wherein the said cells are skin and muscle fibroblasts.

13. A method according to claim 11 wherein the interferon inducing substance is a ds RNA of viral origin.

14. A method according to claim 13 wherein the ds RNA is isolated from virus particles infecting *P. chrysogenum*.

15. In a method for the preparation of a virus in vitro the improvement which comprises contacting a monolayer of animal cells supported on the surface of a solid porous matrix with a liquid medium containing an infective virus, said liquid medium being in the form of a film derived from the breakdown of a foam generated from said liquid medium and a gas leaving gas in the interstitial spaces; and thereafter separating the virus.

16. A method according to claim 15 wherein the virus is Mareks disease virus or Foot and Mouth disease virus.

* * * * *